United States Patent
Spotnitz

[19]

[11] Patent Number: 5,814,066
[45] Date of Patent: Sep. 29, 1998

[54] REDUCTION OF FEMORAL ARTERIAL BLEEDING POST CATHETERIZATION USING PERCUTANEOUS APPLICATION OF FIBRIN SEALANT

[75] Inventor: William D. Spotnitz, Charlottesville, Va.

[73] Assignee: The University of Virginia Patent Foundation, Charlottesville, Va.

[21] Appl. No.: 362,868

[22] Filed: Dec. 23, 1994

[51] Int. Cl.⁶ .................................................. A61B 17/00
[52] U.S. Cl. .................................................. 606/214; 128/898
[58] Field of Search ............................... 606/212–214, 606/1; 128/898

[56] References Cited

U.S. PATENT DOCUMENTS 5,320,639  6/1994  Rudnick ............................ 606/213
5,443,481  8/1995  Lee ................................... 606/214

FOREIGN PATENT DOCUMENTS 482350  4/1992  European Pat. Off. ............. 606/213

*Primary Examiner*—Jeffrey A. Schmidt
*Attorney, Agent, or Firm*—Oblon, Spivak, McClelland, Maier & Neustadt, P.C.

[57] ABSTRACT

Post catheterization arterial bleeding is reduced by introduction of a fibrin sealant, prepared from fibrinogen and thrombin, into the periarterial tissue surround the arteriotomy through which the catheter was inserted. The fibrin sealant is introduced as the catheter is withdrawn, which introduction may be accompanied by local pressure. The fibrin sealant, prepared from fibrinogen and thrombin, clots or "sets" to form a fibrin seal, reducing arterial bleeding and post catheterization difficulties.

6 Claims, 2 Drawing Sheets

REDUCTION OF FEMORAL ARTERIAL BLEEDING POST CATHETERIZATION USING PERCUTANEOUS APPLICATION OF FIBRIN SEALANT

BACKGROUND OF THE INVENTION

Field of the Invention

This invention pertains to a method of reducing arterial bleeding as a result of arterial catheterization. Specifically, fibrin sealant is employed as an aid to reduce post catheterization arterial bleeding and to improve the safety of catheter withdrawal.

BACKGROUND OF THE PROBLEM ADDRESSED

Arterial catheterization is one of the most frequently performed inpatient invasive diagnostic and therapeutic procedures in the United States. Approximately one million procedures were performed in 1988 at an estimated cost of $5,000 per procedure and a hospital length of stay of 3 days. The number of patients undergoing catheterization continues to grow, and the pressure to reduce hospital costs by limiting length of hospital stay is increasing. There are now more frequent efforts to carry out cardiac catheterizations on an outpatient basis. Complications may occur after any catheterization from inadequate hemostasis. These include groin hematomas, cross hemorrhage (1.9%), false aneurysm formation (0.6%), and thrombosis (1%). These complications may require operation (1%) and can contribute significantly to patient morbidity as well as hospital costs and increased lengths of stay. With the use of anticoagulant therapy and large-caliber sheaths required for new, larger intravascular devices, femoral catheterization has been associated with an increased risk of vascular complications. Reversal of heparin anticoagulation to remove groin catheters safely can be associated with a number of significant complications including intravascular coagulation, myocardial infarction, peripheral embolic events, and death. A long period of patient immobilization after the procedures has been necessary to assure hemostasis and reduce the incidence of complications. The period of bed rest, however, makes the procedure more uncomfortable for the patient as well as less efficient in the use of hospital beds and precious financial resources.

SUMMARY OF THE INVENTION

The number of cardiac catheterizations performed yearly is growing with correspondingly increasing amounts of morbidity, complications and hospital costs. This study suggests that fibrin sealant instillation via an arterial sheath at the completion of femoral catheterization may improve hemostasis. Results using fibrin sealant in 12 unheparinized dogs documented significant reductions (McNemar's exact test) versus control for groin ecchymoses (1 versus 8, p=0.008) and radiolabeled hematoma formation (0 versus 7, p=0.16). Also swelling was less in the fibrin sealant treated groins when compared to control groins (1 versus 6, p=0.125) but failed to reach statistical significance. Results in eight heparinized dogs (clotting time 374=22, mean±SEM) revealed a statistically significant reduction in signs of gross bleeding in the fibrin sealant-treated groins (1 versus 8, p=0.016). This method may contribute to reduced morbidity, complications, and length of hospitalization. It may also allow for earlier patient mobilization after cardiac catheterization.

Fibrin sealant is a well-known tissue adhesive which combines fibrinogen and thrombin to form fibrin. This agent has been used in a wide variety of surgical procedures as both a highly effective biological sealant and hemostat. We hypothesized that superior hemostasis at the completion of the catheterization procedure could be achieved by the application of fibrin sealant to the periarterial tissue adjacent to the arteriotomy site. By enhancing and strengthening the normal hemostatic mechanisms, this method allows for earlier patient mobilization and decreased length of hospital stay. This improvement is significant enough to improve the safety of catheter removal in heparin anticoagulated patients.

Figure 1:
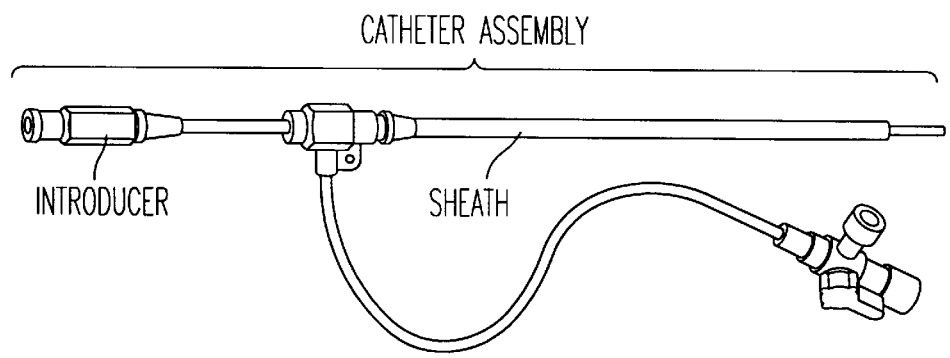
FIG. 1 Catheter assembly including introducer and sheath.
Figure 2:
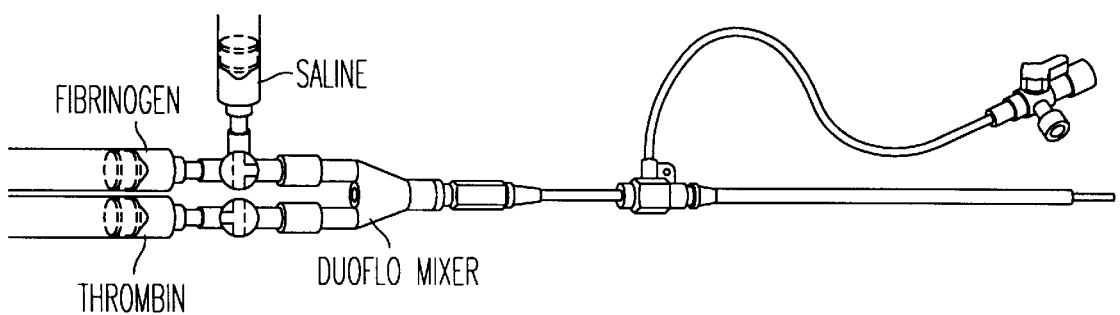
FIG. 2 Catheter assembly attached to mixer, 3-2way stopcocks, and syringes containing saline, fribinogen and thrombin. The introducer has been pulled back so that its tip resides entirely within the body of the sheath.
Figure 3A:
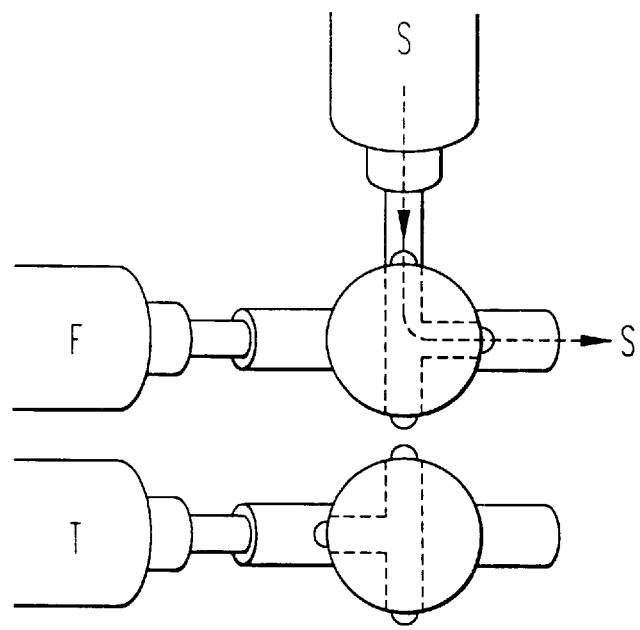
FIGS. 3 A. Orientation of stopcocks for monitoring the catheter position with only the saline syringe open to the introducer lumen.
Figure 3B:
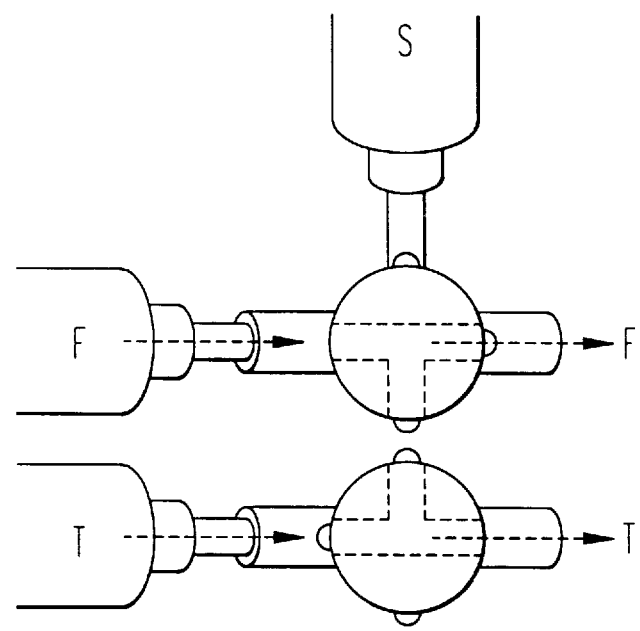

B. Orientation of stopcocks for injection of fibrinogen and thrombin to form fibrin sealant for application through the introducer.

DETAILED DESCRIPTION OF THE INVENTION

Materials and Methods

Animal Preparation

In this study, a canine model was used to assess the safety and efficacy of fibrin sealant in assuring post-procedural femoral arterial hemostasis. Animals were divided into two groups. Group I consisted of 15 unheparinized dogs (26.4±2.1 kg) while group II consisted of nine dogs (27.4±2.5 kg) anticoagulated with heparin. The dogs were cared for in accordance with the "Position of the American Heart Association on Research Animal Use". General anesthesia was induced in fasting mongrel dogs, using intravenous biotol (40 mg/kg) (Bio-Ceutic, St. Louis, Mo.). The animals were intubated and ventilated mechanically with a dual-phase control respirator pump (Model 613, Harvard Apparatus, Dover, Del.). Anesthesia was maintained using a 1% halothane (Holocarbon Laboratories, August, S.C.). Venous access was achieved in the foreleg (20-gauge catheter, Critikon, Johnson & Johnson, Tampa, Fla.) and in the external jugular vein (16-gauge catheter, Critikon, Johnson & Johnson, Tampa, Fla.). Five-hundred milliliters normal (0.9%) saline was administered during the study to ensure adequate animal hydration. In group I dogs, after induction of anesthesia, pyrolite pyrophosphate with stannous chloride (duPont-Merck, Billerica, Mass.) was injected intravenously into each animal in preparation for red blood cell labeling with technetium. Forty minutes from the time pyrolite was administered, 5 ml of arterial blood was withdrawn and labeled with technetium-99 m (Mallinckrodt, St. Louis, Mo.). After shaving and sterile preparation, 4 ml of 1% lidocaine hydrochloride (Abbott Laboratories) was infiltrated into the groin skin and subcutaneous tissues adjacent to each femoral artery. Both arteries were cannulated using size 8F introducers and sheaths (Hemaquet II, 6468, USCI, Tewesburg, Mass.). The femoral sheaths were left in place for 30 minutes.

Preparation of Fibrin Sealant

Fibrin sealant was prepared using a standard two-component technique. Concentrated fibrinogen was obtained from the University of Virginia Hospital Blood Bank. It was prepared from single-donor human plasma, tested for hepatitis B surf ace antigen and core antibody, hepatitis C antibody, HIV I and II antibody, and HTLV I antibody. Four milliliters of this fibrinogen was combined with 4 ml of commercially available bovine thrombin (1,000 NIH units/ml, Johnson & Johnson, Arlington, Tex.) to form fibrin sealant.

Delivery of Fibrin Sealant

In order to achieve good hemostasis at the site of the femoral arterial puncture, it was necessary to instill fibrin sealant into the soft tissue space adjacent to the arteriotomy. However, it was critically important to avoid any intra-arterial injection of the sealant. A safe and reproducible method of delivering the fibrin sealant through a standard catheter system (FIG. 1) was developed. The introducer was placed inside the sheath so that its tip was entirely within the body of the sheath. The other end of the introducer was attached to the fibrin sealant administration assembly. This consisted of two 5-ml syringes; one contained 4 ml of fibrinogen, the other contained 4 ml of thrombin. The syringes were each, in turn, attached to a three-way stopcock, then to a single DuoFlo mixer unit (Hemaedics, Inc., Malibu, Calif.), and finally to the proximal hub end of the introducer. The DuoFlo mixer allowed separate injection of the fibrinogen and thrombin so that both components mixed just prior to traveling through the introducer lumen. A 10-ml syringe, half filled with saline, was also attached to one of the three-way stop-cocks in order to monitor arterial blood pulsations as an indicator of catheter tip position. The whole sheath and introducer assembly was then slowly withdrawn from the artery, and its position, inside or outside the artery, was determined by the presence or absence of arterial pulsations in the saline syringe. When the pulsations ceased, the rip of the sheath was judged to be in the soft tissues adjacent to the artery and no longer within the arterial lumen. Pressure was applied over the arteriotomy site, fibrin sealant was injected, the assembly was fully withdrawn, and manual pressure on the area was continued. On the control side, the femoral sheath was simply withdrawn and manual pressure alone was applied immediately to the area. The side into which the fibrin sealant was injected was randomly chosen so as not to bias the investigators applying pressure to the groin. Manual pressure was continued for 20 uninterrupted minutes. In group I dogs, the groins were examined, and, if hemostasis was not achieved, pressure was reapplied equally to both sides in 5-minute increments until all bleeding had stopped. When hemostasis was reached, manual pressure was discontinued, and 1.36 kg (3 lb.) weights were placed on the groins for 5 minutes while the animal was transferred to the nuclear imaging area. In group II dogs, groin observation for signs of gross bleeding was performed after 20 minutes of manual compression. After observation, heparinization was reversed with protamine (Protamine Sulfate Injection, USP, Elkins-Sinn, Inc, Cherry Hill, N.J.) and followed with at least an additional 20 minutes of compression to any bleeding groin in order to achieve satisfactory hemostasis.

Anticoagulation

Group II dogs were anticoagulated using systemic intravenous boluses of heparin with monitoring of activated clotting times (ACT) every 10 minutes and appropriate repeat heparin dosing. Doses of heparin were chosen to maintain an elevated ACT in the 350 to 400 second range with a mean of 374=22 (mean=SEM) using a previously published algorithm. In both groups I and II, animals were observed in the vivarium for 48 hours after participating in these experiments.

Scintigraphic Imaging Methods

Scintigraphic imaging in group I dogs was performed by a single investigator who was blinded as to which femoral area had been treated with fibrin sealant. The animals were placed supine in a padded Plexiglas cradle under an Anger cameral (Searle Pho-Gamma 37) fitted with a low-energy all-purpose collimator. The camera face was moved close to the groin area. There was a 10-to 14-cm distance separating the right and left catheter insertion sites, and these two puncture sites were identified externally with two point sources (~50 $\mu$CI 99 mTc) in 2 small plastic vials. The exact leg position was recorded to allow consistent repositioning for subsequent images. The marker sources were placed over each femoral sheath insertion site for alignment within the camera field of view. A short (<1 minute) image (128×128 matrix) was obtained to identify the insertion sites on subsequent images. After the marker image was obtained, animals were injected with autologous technetium-labeled red blood cells, (mean=16.65=3.51 mCi), through the external jugular venous cannula. The labeling efficiency of the red blood cells was checked prior to their injection; in all cases it was >90%. The labeled red cells were allowed to circulate systemically for 5 minutes prior to acquiring the next (baseline) image. Two 5-minute images (128×128 matrix) were obtained and stored on an image processing computer (Sophy GX+, Sopha Medical Systems, Columbia, Md.) interfaced with the Anger camera for analysis. One-milliliter reference blood samples were obtained from the foreleg venous cannula at the beginning of each image acquisition period. They were counted using a gamma well counter (Packard) to determine the blood specific activity ($\mu$Ci/ml).

Physical signs

At the same time, in group I dogs, any physical signs (specifically ecchymosis [blue or purplish skin discoloration $\geq$2.5 cm in diameter], swelling [swelling $\geq$2.5 cm in diameter and $\geq$0.5 cm in height], or gross bleeding [required manual compression to stop]) appearing and/or progressing in the femoral areas were noted as an indication of hematoma formation. Group II dogs were observed for bleeding immediately after a period of 20 minutes of manual compression to both groins. At the completion of imaging and observation, both groups I and II dogs had their halothane discontinued and were safely extubated after a suitable period of recovery. Animals were transferred to the vivarium where they were allowed to recover fully and to move about freely for the next 14–16 hours.

Follow-Up Observation

The imaging process was repeated 14–16 hours later in group I dogs after administering a small dose of biotol via the foreleg venous line to achieve a short period of anesthesia without the need for endotracheal intubation. The animals were again placed under the Anger camera as described above. Scintigraphic imaging and blood sampling were repeated exactly as a baseline, and physical signs in the groins were noted again. Anesthesia was discontinued at the end of this imaging session, and the dogs were transferred to the vivarium to recover. After the imaging sequence, all the images were corrected for image non-uniformities using an image of a uniform flood source (>30 million counts) obtained prior to the imaging session. The 5-minute images were reviewed to ensure that no bleeding occurred during the imaging period and were then added to give a single image of 10 minutes in duration. Qualitative analysis of all nuclear images was performed by two independent observers who were blinded as to the site of fibrin sealant injection.

Statistic

Since the effect of fibrin sealant was based on a comparison of control and fibrin sealant-treated groins of the same animal, McNemar's test for correlated proportions was used to compare the rate of success of the fibrin sealant treated versus control groins. In addition, because the sample size was limited, an asymptotic chisquare distribution could not be assumed when applying McNemar's test. As a result, a Fisher-like exact test was used to evaluate statistical significance. All hypothesis testing was two-sided and based on a 0.05 level of significance.

RESULTS

Exclusions

In group I, three experimental animals were excluded during 15 experiments. This was due to continued bleeding from the control arterial puncture site despite a prolonged period for manual pressure producing an unstable baseline in one animal. There were technical difficulties in injecting the fibrin sealant resulting in a minimal volume of fibrin sealant reaching the periarterial soft tissue in two animals. Twelve animals were available for final analysis in group I. In group II, one experimental animal was excluded from a total of nine experiments. This was due to use of improper group compression technique. Eight animals were available for final analysis in group II.

Scintigraphic Image Analysis

To illustrate scintigraphic images in group I dogs, a normal (no bleeding) study was conducted. A stable baseline image was obtained with both femoral arteries identified. The same dog was imaged 16 hours later, and even though the image intensity was less than that at baseline owing to loss of radioactive counts (99 mTc decay and radiolabeled blood cell sequestration), it was still obvious that no bleeding and/or hematoma formation had occurred in either femora area. Another dog had a stable baseline image, but 16 hour later the image showed a definite and significant increase in extravascular count density, indicating a hematoma around the left femoral artery. The right groin (fibrin sealant treated) was stable and devoid of hematoma. Of the 12 group I animals studied, none had a hematoma in the groin injected with fibrin sealant, whereas seven control areas had definite hematoma formation (P=0.016). All animals with scintigraphic findings of hematoma formation had physically detected signs of local swelling. None of the animals required surgical intervention to evacuate the hematoma.

Physical Signs

Ecchymoses occurred in eight control groins but in only one of the groins treated with fibrin sealant (P=0.008). In three dogs, the ecchymoses appeared early on the control side, and progressed further by the time the second set of nuclear images were obtained. All three of these dogs had a hematoma on the same side as the early ecchymoses. Only one dog exhibited late ecchymosis without hematoma formation on the control side. Swelling took place in six control groins but in only one fibrin sealant-injected groin (P=0.125). The swelling in the fibrin sealant-treated groin occurred early but was small. Thus, swelling was no longer present at the time of second observation (16 hours later). Swelling occurred early in five of the control areas and progressed in three of these. One control groin had only late swelling. All six control swollen groins were associated with hematoma development. No gross external bleeding occurred in any of the animals. Additional manual pressure was required to achieve adequate hemostasis as a result of bleeding in one treated and four control groins (P=0.3). Overall pressure was applied for a total of 20–58 minutes (mean=24.8±10.9 minutes).

In group II dogs, signs of bleeding were grossly obvious and consisted of rapid massive swelling and/or free hemorrhage. As seen in Table II, all eight control groins exhibited signs of bleeding and only one fibrin sealant-treated side showed evidence of local hemorrhage (P=0.016) after 20 minutes of manual compression.

No animals in group I or II ever exhibited signs of arterial occlusion or distal embolization of fibrin sealant.

DISCUSSION

Human Stimulation

The model was specifically designed to simulate routine cardiac catheterization in human patients. For this reason, lidocaine was infiltrated into the subcutaneous tissues as during human femoral catheterization even though the animals were given general anesthesia as designated in the animal care committee approved protocol. In addition, the catheters were left in place for 30 minutes, approximately the time required for routine diagnostic catheterization. Groin pressure was applied simultaneously and bilaterally for 20 minutes after catheter removal and in group I equally beyond 20 minutes as required to obtain gross hemostasis as during human cardiac catheterization. The fibrin sealant used has been employed in other application and indications clinically at our institution in more than 2,500 patients since 1985. It consisted of commercially available bovine thrombin and concentrated human fibrinogen as obtained from the University of Virginia Hospital Blood Bank. The fibrinogen was obtained as single donor units and was prepared under methods previously published; it was designed to meet standards for maintenance of a closed system as well as to avoid waste of valuable unstable clotting factors found in routine cryoprecipitate. The groin catheterization fibrin sealant delivery system used called for standard sheaths and introducers presently in clinical use. Relatively large size 8F sheaths were chosen in this dog model to create significant arterial injury and increase the degree of difficulty in achieving hemostasis. Group II dogs were anticoagulated with systemic heparin to further increase the difficulty of achieving hemostasis.

Measure Bleeding Parameters

Four parameters of hemorrhage were monitored in group I dogs. Two of the parameters, radiolabeled hematoma formation and ecchymoses, provided strong statistically significant evidence in favor of the benefits of fibrin sealant. A third parameter, swelling, just missed statistical significance. It may have achieved significance with a larger sample size. All seven animals in group I with swelling also had ecchymosis, suggesting good concordance between these measurements, but one parameter, gross bleeding, was not present at any time in any of the 12 group I animals included in this study. In group II animals evidence of gross bleeding was evident in all eight control groins and in one fibrin sealant-treated groin. These data suggest that fibrin sealant may be an effective method for achieving prolonged hemostasis following femoral artery catheterization in a canine model.

Mechanism of Fibrin Sealant Remostasis

The mechanism of fibrin sealant hemostasis was evaluated in four unheparinized dogs. These animals were euthanized at the end of a standard protocol achieving hemostasis after 20 minutes and had the treated femoral vessels excised as a block. Tissue was fixed in formalin and stained with hematoxylin and eosin revealing a fibrin patch on the outside of the artery at the site of the catheter-induced injury.

Complications

No specific complications were encountered in the animals in this report. All animals recovered from anesthesia and there was no evidence of vascular compromise to the lower extremities on either the control or fibrin sealant-treated sides. No false aneurysms, massive delayed bleeding, arteriovenous fistulas, thromboses, or emboli were noted with in 48 hours of catheterization.

Human Applications

The inventive technique may allow for early mobilization of human patients after cardiac catheterization. The advantages of this technique may include reductions in discomfort associated with prolonged bed rest and groin sandbag placement as well as reductions in hospitalization due to the need for inpatient monitoring and overnight observation after catheterization. Some of the complications of femoral catheterization as well as complications associated with heparin anticoagulation reversal may be reduced by fibrin sealant-enhanced hemostasis.

Fibrin Sealant Risks

The fibrin sealant system itself can be associated with several complications including embolization. However, using the methods in this report for confirming the position of the groin sheaths outside of the femoral arteries at the time of sealant instillation avoided this serious complication. Fibrin sealant does carry at least a theoretical risk of viral disease transmission. This danger can be eliminated by using autologous fibrinogen. Other future solutions including sophisticated modern techniques for viral inactivation or the use of recombinant genetic engineering to synthesize the components of fibrin sealant. There are recent reports that repeated exposures to bovine thrombin can lead to antibody production which may produce significant coagulation abnormalities. These problems could be eliminated using recombinant thrombin, which may become clinically available in the near future.

This invention has been disclosed in terms of both generic description and specific example. Variations will occur to those of skill in the art, particularly in the origin and composition of fibrin sealant, without inventive thought. Such variations remain within the scope of the invention, save as excluded by the recitations of the claims below.

What is claimed is:

1. A method for reducing arterial bleeding following arterial catheterization of a patient, comprising introducing fibrin sealant to periarterial tissue adjacent an arteriotomy site in which a catheter has been inserted, withdrawing said catheter at the same time said fibrin sealant is introduced and allowing said fibrin sealant to form a fibrin seal, wherein precursors of said fibrin sealant are separately introduced into a conduit with an opening at said periarterial tissue, such that said fibrin sealant precursors are mixed prior to delivery to said periarterial tissue.

2. The method of claim 1, wherein pressure is applied to the area where said fibrin sealant has been introduced after said withdrawal of said catheter.

3. The method of claim 2, wherein said pressure is maintained until hemostasis is achieved in said patient.

4. The method of claim 1, wherein said fibrin sealant comprises fibrinogen and thrombin.

5. The method of claim 4, wherein said fibrinogen and said thrombin are separately introduced into a conduit with an opening at said periarterial tissue, such that said fibrinogen and thrombin are mixed prior to delivery to said periarterial tissue.

6. The method of claim 1, wherein said patient is has been treated with heparin to reduce clotting prior to the step of introducing said fibrin sealant.

* * * * *